United States Patent [19]

Mushahwar et al.

[11] Patent Number: 5,895,750
[45] Date of Patent: Apr. 20, 1999

[54] IMMUNOASSAY FOR THE DETECTION OF LIGANDS

[75] Inventors: Isa K. Mushahwar, Waukegan; Richard H. Decker, Deerfield; Karen V. Stuckmann, Morton Grove, all of Ill.

[73] Assignee: Abbott Laboratories, Abbott Park, Ill.

[21] Appl. No.: 08/434,251

[22] Filed: May 3, 1995

Related U.S. Application Data

[63] Continuation of application No. 08/196,885, Feb. 10, 1994, abandoned, which is a continuation of application No. 07/996,867, Dec. 16, 1992, abandoned, which is a continuation of application No. 07/687,785, Apr. 19, 1991, abandoned, which is a continuation of application No. 07/418,981, Oct. 6, 1989, abandoned, which is a continuation of application No. 07/070,647, Jul. 6, 1987, abandoned, which is a continuation of application No. 06/608,849, May 10, 1984, abandoned.

[51] Int. Cl.$^6$ .................................................. G01N 33/53
[52] U.S. Cl. .......................... 435/7.5; 435/5; 435/6; 435/7.9; 435/7.23; 435/7.92; 435/7.93; 436/518
[58] Field of Search ................... 435/5, 6, 7.23, 435/7.32, 7.5, 7.9, 7.92, 7.93, 804; 436/501,518, 530

[56] References Cited

U.S. PATENT DOCUMENTS

| | | | |
|---|---|---|---|
| 4,228,237 | 10/1980 | Hevey et al. | 435/7 |
| 4,535,057 | 8/1985 | Dreesman et al. | 435/7 |
| 4,687,732 | 8/1987 | Ward et al. | 435/6 |
| 4,945,042 | 7/1990 | Geiger et al. | |

FOREIGN PATENT DOCUMENTS

B-82573  10/1982  Australia.

OTHER PUBLICATIONS

Brigati, et al., *Biological Abstracts* 76:5025 (Abstract No. 46212) (1983).
J.L. Guesdon, et al., *J. Histochem. & Cytochem.* 27(8):1131–1139 (1979).
M. Wilchek and E.A. Bayer, *Immunology Today* 5(2) 39–43 (Mar., 1984).
D.J. Brigati et al., *Virology* 126:32–50 (1983).
E.A.Bayer and M. Wilchek, *Methods and Biochemical Analysis* 26:1–45 (1980).
P.R. Langer–Safer et al., *Proc. Natl. Acad. Sci.* 79: 4381–4385 (1982).
I.K. Mushahwar et al. *J Virol. Methods* 16:45–54 (1987).
P. Vincent, et al., *Journal of Immunological Methods* 165 (1993) 177–182.
Wood et al. *J. Histochem. Cytochem.*, 29(10):1196–1204 (1981).
Banerjee et al. *J. Clin. Pathol.*, 37: 223–225 (1984).
Federation Proceedings, 46, Abstract 4911, p. 1159 (1987) Mock.
Langer P. et al., *An Immunological Method of Gene Mapping by In Situ Hybridization* (undated).
Langer P. et al., Enzymatic synthesis of biotin–labeled polynucleotides: Novel nucleic acid affinity probes, in *Proc. Natl. Acad Sci. U.S.A* vol. 78, No. 11 pp. 6633–6637, Nov. 1981.

*Primary Examiner*—Toni R. Scheiner
*Attorney, Agent, or Firm*—Dianne Casuto; Priscilla E. Porembski

[57] ABSTRACT

A biotin-antibiotin immunoassay comprises coating a solid phase with a ligand-specific binding material, reacting the solid phase with a test sample, reacting the solid phase with the biotin-labeled form of the ligand-specific binding material and antibiotin labeled with a suitable marker. The marker is then measured to detect the amount of ligand present in the test sample.

21 Claims, No Drawings

IMMUNOASSAY FOR THE DETECTION OF LIGANDS

This application is a continuation application of Ser. No. 08/196,885 filed Feb. 10, 1994 (now abandoned), which is a continuation of Ser. No. 07/996,867 filed Dec. 16, 1992 (now abandoned), which is a continuation application of Ser. No. 07/687,785 filed Apr. 19, 1991 (now abandoned), which is a continuation application of Ser. No. 07/418,981 filed Oct. 6, 1989 (now abandoned), which is a continuation application of Ser. No. 07/070,647 filed Jul. 6, 1987 (now abandoned), which is a continuation application of Ser. No. 06/608,849 filed May 10, 1984 (now abandoned).

TECHNICAL FIELD

The invention relates to immunoassays for the detection of ligands. More particularly, the invention relates to sensitive and specific immunoassays which utilize a biotin-antibiotin interaction.

BACKGROUND OF THE INVENTION

Prior assay techniques for detecting ligands in a specimen have utilized the strong but noncovalent interaction between biotin and the highly basic protein avidin. In one such assay, described by Guesdon et al., *J. Histochem. Cytochem.* 27, 8:1131–1139 (1979), known as the Bridged Avidin-Biotin (BRAB) technique, a test sample such as serum containing an unknown antigen or antibody is reacted with a solid phase coated with the corresponding antibody or antigen. The test sample is then reacted with a biotinylated protein form of the same antigen or antibody used to coat the bead. This "sandwich" is then reacted with free avidin and a biotin-labeled indicator enzyme. The enzyme activity measured is directly proportional to the amount of unknown antigen or antibody present in the serum sample.

The BRAB technique described above has several limitations. The highly basic avidin carries a high positive charge and can nonspecifically adsorb to any negatively-charged biological components in the assay. The catalytic activity of the indicator enzymes can be destroyed or reduced upon conjugation to biotin. Also, this method can not be easily adapted to inhibition-type assays because of steric considerations.

A variation of the BRAB technique consists of coating a solid phase with antigen or antibody, reacting the coated solid phase with test serum, and reacting the test serum with a conjugate of avidin and antigen or antibody. The test serum is then reacted with a biotin-labeled indicator enzyme. This assay technique has the same disadvantages as the BRAB method, and, in addition, it is difficult to synthesize and obtain acceptable yields of avidin-antigen or avidin-antibody conjugates. Also, some immunological reactivity of the antigen or antibody is lost upon forming a conjugate with avidin.

In U.S. Pat. No. 4,228,237, another biotin-avidin assay is described in which an enzyme-labeled avidin and a biotin-labeled reagent are utilized. In this assay, a solid phase containing a specific binding substance for a ligand of interest is incubated with a liquid medium suspected of containing the ligand of interest. Next, a biotin-labeled specific binding substance for the ligand and an enzyme-labeled avidin are added. Alternatively, the biotin-labeled specific binding substance for the ligand is bound to the enzyme-labeled avidin. The unreacted reagents are separated from the insoluble phase after incubation, and the enzyme activity of either the insoluble phase or the separated unreacted reagents is determined as a measure of the amount of ligand in the liquid medium.

This method has the same limitations as described above for the BRAB method such as the nonspecific binding of the highly positively-charged avidin. Also, the avidin-enzyme complex is not very stable, particularly when the complex is of a high concentration or at temperatures above 37° C.

DESCRIPTION OF THE INVENTION

The term "ligand" as used in the present invention refers to antigens, antibodies, haptens, hormones and their receptors, deoxyribonucleic acid and other organic substances for which a specific-binding material can be provided.

Representative ligands which can be determined by methods of the present invention are viral, bacterial, fungal, rickettsial, and tumor-associated antigens and their corresponding antibodies and deoxyribonucleic acid. The term "test sample" as used herein refers to biological fluids including human biological fluids such as human serum, plasma or urine.

The term "reagent(s)" as used herein refers to any of the components to be added in the steps of an immunoassay. Such reagents include, for example, a biotin-labeled ligand-specific binding material and antibiotin labeled with a marker.

According to the invention, a direct or inhibition-type biotin-antibiotin immunoassay is provided which is sensitive and specific, and which is not subject to the disadvantages of a biotin-avidin immunoassay. The direct biotin-antibiotin assay comprises first immobilizing a ligand-specific binding material onto a solid phase such as a bead, test tube, microtiter plate, nitrocellulose sheet or derivatized paper. The solid phase is then reacted with a test sample, such as human serum containing the ligand to be detected. Next, the solid phase is reacted with a biotin-labeled form of the ligand-specific binding material and antibiotin labeled with a suitable marker. Examples of suitable markers include enzymes, radioisotopes, and other reagents which provide measurable activity such as colorimetric or fluorometric activity or radioactivity.

Next, the solid phase and the unreacted reagents of the assay are separated and the presence of the marker is measured in either the solid phase or the unreacted reagents. If enzyme-labeled antibiotin is used, a soluble substrate for the enzyme is added, and the enzyme's conversion from a colorless precursor to a colored product is measured spectrophotometrically. The amount of color produced is directly proportional to the amount of ligand present in the test sample.

Alternatively, an inhibition-type immunoassay can be performed utilizing the concepts of the present invention. In the inhibition-type assay a ligand-specific binding material is immobilized onto a solid phase, and the solid phase is reacted with a test sample containing the ligand to be detected. This is followed by addition of the biotin-labeled form of the ligand and antibiotin labeled with a suitable marker. In the inhibition-type assay, the amount of marker present in either the solid phase or in the unreacted reagents is inversely proportional to the amount of ligand present in the test sample.

Both the direct and inhibition-type biotin-antibiotin immunoassays can be performed in a three-step, two-step or one-step procedure. In the three-step procedure for the direct biotin-antibiotin immunoassay, the first step comprises incubating a solid phase coated with ligand-specific binding material with a test sample containing an unknown amount of ligand. The solid phase is washed, and in the second step, the solid phase is incubated with a biotin-labeled form of the ligand-specific binding material. The solid phase is washed a second time, and then in the third step, the solid phase is incubated with antibiotin labeled with a suitable marker. The marker present in the solid phase or in the unreacted reagents is then measured to detect the amount of ligand present in the test sample.

The two-step procedure comprises the same first step as described for the three-step procedure. The second step comprises the simultaneous addition of the biotin-labeled form of the ligand-specific binding material and the labeled antibiotin.

The one-step procedure involves the simultaneous addition of test sample, biotin-labeled ligand-specific binding material and labeled antibiotin for one incubation period.

The principals of the biotin-antibiotin immunoassay are especially useful in an immunoassay for the detection of antibody to Hepatitis B surface antigen (anti-HBs). However, the biotin-antibiotin immunoassay can also be utilized for the detection of many other viral, bacterial, fungal, rickettsial and tumor-associated antigens and their corresponding antibodies. The biotin-antibiotin system is also useful in detecting deoxyribonucleic acid in an immunoassay.

The following examples are intended to illustrate the invention and not to limit its scope or spirit.

EXAMPLE I

This example demonstrates a three-step direct immunoassay for the detection of antibody to Hepatitis B surface antigen (anti-HBs).

A polystyrene bead coated with Hepatitis B surface antigen (HBsAg), according to techniques described by Jilg et al., *J. Med. Virol.* 13:171–178 (1984), is incubated for 18–22 hours at room temperature with a human serum sample containing an unknown amount of anti-HBs. The bead is then washed with deionized water and incubated with biotin-labeled HBsAg for two (2) hours at 40° C. The bead is washed a second time and then incubated with either $^{125}$I- or horseradish peroxidase-labeled antibiotin (either monoclonal or polyclonal) for two (2) hours at 40° C. The bead is washed a third time, and if horseradish peroxidase-labeled antibiotin is utilized, a peroxidase substrate, such as o-phenylenediamine, is added to produce a yellow-colored product. The amount of color is then determined spectrophotometrically as a measure of the amount of anti-HBs in the test sample. If $^{125}$I-labeled antibiotin is utilized, radioactivity is measured as the amount of anti-HBs present in the test sample.

EXAMPLE II

This example illustrates a two-step immunoassay for the detection of anti-HBs.

A polystyrene bead coated with HBsAg is incubated with a serum sample and washed as described in Example I. Next, biotin-labeled HBsAg and $^{125}$I- or horseradish peroxidase-labeled antibiotin are added simultaneously to the bead and incubated for two (2) hours at 40° C. Color is developed and measured or radioactivity is determined as described in Example I.

EXAMPLE III

This example demonstrates a one-step immunoassay for the detection of anti-HBs.

A polystyrene bead coated with HBsAg is incubated with a serum sample, biotin-labeled HBsAg and $^{125}$I- or horseradish peroxidase-labeled antibiotin for 18 to 22 hours at room temperature. Color or radioactivity are determined as described in Example I.

EXAMPLE IV

This example demonstrates the preparation of biotin-labeled HBsAg.

Biotinyl-N-hydroxysuccinimide (BNHS, 0.27 micromoles) dissolved in distilled dimethylformamide is added to 800 micrograms of HBsAg in 1 ml of a buffer comprising 100 mM $KH_2PO_4$, pH 8.0 containing 100 mM NaCl. The solution is mixed vigorously and rotated for 18 to 22 hours at 4° C., followed by dialysis against the same buffer for 18 to 22 hours at 4° C.

EXAMPLE V

This example illustrates a method of preparing polyclonal antibiotin antibodies in rabbits.

Rabbits are immunized with biotinylated bovine serum albumin (biotinylated-BSA) produced as described above for HBsAg-biotin. When the antibody concentrations reach peak titers, the rabbits are sacrificed.

The antibiotin antibodies are purified from rabbit serum by a two-step process. First, the serum is circulated over an affinity column with BSA as the ligand to remove anti-BSA antibodies. In the second step, the anti-BSA-free serum is passed over an affinity column with Biotin-BSA as the ligand to selectively remove antibiotin. Subsequently the antibiotin is eluted by a chaotropic reagent.

EXAMPLE VI

This example illustrates a method of preparing monoclonal antibiotin antibodies in mice.

Mice are immunized with biotinylated-BSA, and mice with high titers of antibiotin antibodies are sacrificed. Lymphocytes from splenic tissues of the sacrificed mice are fused with BALB/c SP 2/0 myeloma cells according to the procedure described by Galfrie, et al., *Nature* 226:550–552 (1977). The resultant antibiotin clones are screened by direct and indirect assays to determine antibiotin-positive clones. The positive clones are grown in mice as ascitic tumors, and the monoclonal antibiotin antibodies are purified and separated from the ascites fluid by ion exchange chromatography.

Both the polyclonal and monoclonal antibiotin antibodies can be conjugated to horseradish peroxidase according to the method of Nakane, et al., *J. Histochem. Cytochem.* 22:1084–1091 (1974), or labeled with $^{125}$I according to the method of Greenwood, et al., *J. Biochem.* 89:114–123 (1963).

There are many advantages to the biotin-antibiotin immunoassay. First, this immunoassay is more specific and sensitive than previous biotin-avidin assays since the immunochemical and immunological activity of the reagents are not disturbed by conjugation procedures, and since non-specific interactions between the highly positively charged reagents such as avidin and negatively charged assay components are avoided. Second, the reagents for the inventive immunoassay, including the biotin-labeled ligand-specific binding materials and the $^{125}$I- or enzyme-labeled antibiotin are very stable and have increased shelf lives over the component reagents of a biotin-avidin immunoassay, especially at higher temperatures and concentrations of the reagents. Third, excellent yields of antibiotin antibodies can be obtained for the inventive assay. Fourth, the inventive immunoassay can be utilized for an inhibition-type assay and in one, two or three-step procedures. Fifth, the inventive assay gives well-defined readings of positive and negative samples, and offers better quantification of unknown ligands. There are still other advantages which will be apparent to those skilled in the art.

Although this invention has been described with respect to specific modifications, the details thereof are not to be construed as limitations, for it will be apparent that various equivalents, changes and modifications may be resorted to without departing from the spirit and scope of the invention; therefore, it is understood that such equivalents are intended to be included herein.

What is claimed is:

1. An immunoassay for detecting a ligand comprising:
   a) immobilizing a ligand-specific binding material onto a solid phase;
   b) reacting the solid phase with a test sample;
   c) reacting the solid phase with a biotin-labeled ligand-specific binding material;
   d) reacting the solid phase with antibiotin labeled with a marker;
   e) separating unreacted reagents from the solid phase; and
   f) measuring the amount of the marker in the solid phase or in the unreacted reagents to detect the amount of ligand present in the sample.

2. The immunoassay of claim 1 wherein the marker is an enzyme.

3. The immunoassay of claim 1 wherein the marker is a radioisotope.

4. The immunoassay of claim 1 wherein steps (b), (c) and (d) are performed simultaneously.

5. The immunoassay of claim 1 wherein steps (c) and (d) are performed simultaneously.

6. The immunoassay of claim 1 wherein the ligand is an antigen.

7. The immunoassay of claim 1 wherein the ligand is an antibody.

8. The immunoassay of claim 1 wherein the ligand is selected from the group consisting of viral, bacterial, fungal, rickettsial and tumor-associated antigens and their corresponding antibodies.

9. The immunoassay of claim 1 wherein the ligand-specific binding material is hepatitis B surface antigen.

10. The immunoassay of claim 1 wherein the solid phase is selected from the group consisting of polystyrene beads, test tubes, microtiter plates, nitrocellulose sheets, and derivatized paper.

11. An immunoassay for detecting a ligand comprising:
    a) immobilizing a ligand-specific binding material onto a solid phase;
    b) reacting the solid phase with a human biological fluid;
    c) reacting the solid phase with a biotin-labeled ligand;
    d) reacting the solid phase with an enzyme-labeled antibiotin;
    e) separating unreacted reagents from the solid phase; and
    f) measuring amount of the enzyme in the solid phase or in the unreacted reagents to detect the amount of ligand present in the human biological fluid.

12. The immunoassay of claim 11 wherein the ligand is an antibody to hepatitis B surface antigen.

13. The immunoassay of claim 11 wherein the solid phase comprises a polystyrene bead, test tube, microtiter plate, nitrocellulose sheet or derivatized paper.

14. An immunoassay for detecting a ligand which may be present in a biological fluid test sample, comprising:
    (a) reacting the test sample with a solid phase to which a ligand-specific binding material has been immobilized;
    (b) reacting said solid phase with a biotin-labeled specific binding material;
    (c) reacting said solid phase with antibiotin labeled with a marker;
    (d) separating unreacted reagents from the solid phase;
    (e) measuring the amount of the marker in the solid phase or in the unreacted reagents to detect the amount of ligand present in the sample.

15. The immunoassay of claim 14 wherein the marker is selected from the group consisting of an enzyme and a radioisotope.

16. The immunoassay of claim 14 wherein steps (a), (b) and (c) are performed simultaneously.

17. The immunoassay of claims 14 wherein steps (b) and (c) are performed simultaneously.

18. The immunoassay of claim 14 wherein the solid phase is selected from the group consisting of polystyrene beads, test tubes, microtiter plates, nitrocellulose sheets, and derivatized paper.

19. A competitive immunoassay for detecting a ligand which may be present in a biological fluid sample, comprising:
    (a) reacting the test sample with a solid phase to which a ligand-specific binding material has been attached, a biotin-labeled ligand and antibiotin labeled with a marker;
    (b) separating unreacted reagents from the solid phase;
    (c) measuring the amount of the marker in the solid phase or in the unreacted reagents to detect the amount of ligand present in the sample.

20. The immunoassay of claim 19 wherein the marker is selected from the group consisting of an enzyme and a radioisotope.

21. The immunoassay of claim 19 wherein the solid phase is selected from the group consisting of polystyrene beads, test tubes, microtiter plates, nitrocellulose sheets, and derivatized paper.

* * * * *